United States Patent [19]

Cederholm et al.

[11] Patent Number: 5,139,932
[45] Date of Patent: Aug. 18, 1992

[54] METHOD AND A KIT FOR THE DIAGNOSIS OF IGA NEPHROPATHY

[75] Inventors: Bo Cederholm; Jörgen Wieslander; Per Bygren; Dick Heinegård, all of Lund, Sweden

[73] Assignee: BioCarb AB, Lund, Sweden

[21] Appl. No.: 431,546

[22] PCT Filed: May 9, 1988

[86] PCT No.: PCT/SE88/00240
§ 371 Date: Jan. 8, 1990
§ 102(e) Date: Jan. 8, 1990

[87] PCT Pub. No.: WO88/08983
PCT Pub. Date: Nov. 17, 1988

[30] Foreign Application Priority Data

May 8, 1987 [SE] Sweden .................... 8701905

[51] Int. Cl.⁵ .............. G01N 33/53; G01N 33/564
[52] U.S. Cl. ........................... 435/7.9; 435/7.94; 435/7.95; 435/975; 435/968; 436/507; 436/513; 436/518; 436/808
[58] Field of Search ............ 435/7.9, 7.94, 975; 436/506, 507, 508, 509, 518, 536, 808, 800, 804, 811

[56] References Cited

PUBLICATIONS

Cederholm et al,. "Patients with IgA nephropathy have circulating anti-basement membrane antibodies reacting with structures common to collagen I, II, and IV", Proc. Natl. Acad. Sci. USA vol. 83 pp. 6151–6155 (Aug. 1986).

Rogue-Barreira et al., "Jacalin:An IgA binding lectin" J. Immuno., vol. 134(3) pp 1740–1743 (Mar. 1985).

*Primary Examiner*—Ester L. Kepplinger
*Assistant Examiner*—Carol E. Bidwell
*Attorney, Agent, or Firm*—Gordon W. Hueschen

[57] ABSTRACT

A method for the diagnosis of IgA nephropathy using a specific binding reaction comprising the steps:

a) preparing a substrate capable of binding fibronectin or IgA b) contacting the substrate resulting from step a) with a sample of body fluid drawn from a patient subject to diagnosis to bind any fibronectin-IgA-complex present in said sample to the substrate, and c) determining the presence of complex bound to the substrate using the reaction between the exposed part of such bound complex and a corresponding antibody thereto; and a diagnostic kit for use in such diagnosis.

11 Claims, 3 Drawing Sheets

METHOD AND A KIT FOR THE DIAGNOSIS OF IGA NEPHROPATHY

The present invention relates to a method for the diagnosis of IgA nephropathy using an antigen-antibody interaction, and the invention also includes a diagnostic kit for use in such a diagnosis.

Patients with primary IgA nephropathy, also known as Berger's disease, have been shown to have circulating IgA antibodies, binding to collagen IV prepared from glomerular basement membrane (GBM) (1). It was also shown that the IgA antibodies bound equally well to collagen I, II and IV and that denatured collagens bound antibodies most efficiently (1). In view of the wide distribution of the various collagens, it is of interest to note the coexistence with IgA nephropathy of symptoms from extrarenal organs (2). Thus symptoms from skin, eye and joints are of particular interest since these structures contains collagen as a major component. Indeed one study reports presence of vascular IgA deposits in skin from patients with IgA nephropathy (3).

The association of exacerbations of clinical disease with upper respiratory tract or gastrointestinal infections and the finding of IgA deposits in the glomerular mesangium is well known. The finding of increased levels of IgA-bearing peripheral lymphocytes (4) as well as decreased IgA-specific suppressor T cell activity (5) and increased IgA-specific helper T-alfa cells (6) suggests an immunological mechanism.

Fibronectin, also known as cold insoluble globulin (CIq), that is altered in many disease processes, is present both as a plasmaprotein and as a cell surface protein. The two forms differ slightly in composition but share important functions as binding to gelatin (collagen), heparin, fibrin and cell surface receptors (7). Fibronectin is the major plasma component binding to gelatin (8) and this property as well as its heparin binding properties have been utilized in its isolation (9). Interestingly fibronectin is present also in basement membranes. It can be visualised by immunofluorescense not only in the glomerular basement membrane but also in the mesangium of healthy individuals (10). Furthermore a concomitant increase of mesangial fibronectin and mesagial matrix was observed in patients with IgA nephropathy and Henoch-Schönleins purpura (10).

The present invention is based on the surprising discovery, that the IgA-antibodies are present in circulating immune complexes in patients with primary IgA nephropathy together with fibronectin, and this unexpected finding does, of course, explain the fact that the IgA-containing complexes have the ability of binding to collagen. This new finding that the circulating immune complex contains, in addition to IgA, also fibronectin, enables the provision of both a method for the diagnosis of IgA nephropathy and a diagnostic kit for use in such diagnosis.

Accordingly, one object of the present invention is to provide a method for the diagnosis of IgA nephropathy using antigen-antibody interaction, and another object of the invention is to provide a diagnostic kit for use in such diagnosis of IgA nephropathy.

The method of the present invention is characterized by the following steps:
a) preparing a substrate capable of binding fibronectin or IgA
b) contacting the substrate resulting from step a) with a sample of body fluid drawn from a patient subject to diagnosis to bind any fibronectin-IgA-complex present in said sample to the substrate, and
c) determining the presence of complex bound to the substrate using the reaction between the exposed part of such bound complex and a corresponding antibody thereto.

In preparing such substrate capable of binding fibronectin preferred binding agents are collagen, heparin, fibrin or anti-fibro nectin. According to this aspect of the invention the substrate is prepared in such a way as to bind the fibronectin-IgA-complex through its fibronectin component. This in turn means that the IgA-component of the complex is available for determining the presence of complex bound to the substrate.

On the other hand the binding of the fibronectin-IgA-complex to the substrate can be directed to the IgA-part of the complex. In such case there can be used as a binding agent either anti-IgA or a lectin, both of which are capable of binding IgA. In this case the fibronectin part of the complex will be available for determining the presence of complex bound to the substrate.

The determination under step c) of the method of this invention can be of a quantitative nature and can be based on a conventional detection system. Among such detection systems there may be mentioned those based on enzymatic activity, or systems based on radiation emitted by a radioactive isotope or based on fluorescence.

The substrate used in binding the fibronectin-IgA-complex present in a sample subject to diagnosis can be constituted by different objects, such as microtiter plates, laboratory test tubes, nitro-cellulose paper, plastic spheres or any other object suitable for the purpose.

Samples of body fluid drawn from a patient subject to the diagnostic method of the present invention may be constituted by for example human blood, serum, plasma or saliva.

The invention also provides for a diagnostic kit for use in the diagnosis of IgA nephropathy, and such kit comprises:
a) an object capable of a binding fibronectin or IgA, and
b) reagent comprising a component which is capable of binding IgA or fibronectin and a detection component enabling determination of fibronectin-IgA complex bound to the said object.

In the embodiments wherein the IgA part constitutes exposed part of the complex the object carries attached to the surface thereof heparin, collagen, fibrin or anti-fibronectin. In such case the reagent preferably comprises lectin or antibody directed against IgA.

In the opposite case, wherein fibronectin is the exposed part of the complex the object carries attached to the surface thereof anti-IgA or lectin, the reagent comprising heparin, collagen, fibrin or anit-fibronectin.

In such diagnostic kit according to the invention the function of the detection component may be based on enzymatic activity, radiation emitted by a radioactive isotope or fluorescence.

EXAMPLE 1

Antisera

Figure 1A:
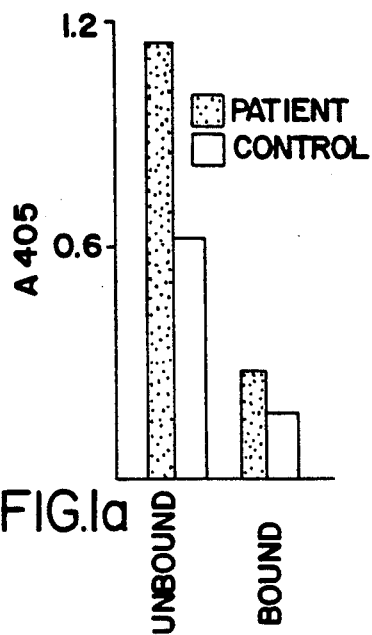
FIG. 1a shows the binding of IgA to a heparin-Sepharose column.

Patient sera were from patients with primary IgA nephropathy (glomerulonephritis and dominating mesangial IgA deposits detected by immunofluorescense microscopy of renal biopsy specimens). None of the patients had signs of systemic lupus erythematosus (SLE), Henoch-Schönleins purpura or cirrhotic liver disease. Sera from healthy blood donors were used as controls.

EXAMPLE 2

Isolation of immune complexes

Antisera (1 ml) were dialysed against 0.05M Tris, 0.05% sodium azide pH 7.4 before applied to a 10 ml Heparin-Sepharose CL-6B column (Pharmacia, Uppsala, Sweden). Material eluted from the column with 0.5M NaCl in the same buffer was dialysed against 0.1M sodium phosphate, 0.05% sodium azide pH 7.5 before chromatographed on a 1 ml Mono Q column (Pharmacia). Chromatography was performed using a LKB (Bromma, Sweden) HPLC system with low pressure mixing. Absorbance was measured at 280 nm with a LKB 2151 variable wavelength detector. Fractions binding to collagen I and reacting with anti human IgA (Dakopatts, Hägersten, Sweden) were pooled and applied to a jacaline a (Pierce chemicals, Rockford, Ill.). IgA containing complexes were eluted with 0.2M melibiose in a buffer containing 0.05M Tris, 0.15M NaCl, 0.05% sodium azide pH 7.5.

EXAMPLE 3

Preparation of collagen I

Collagen I was prepared by pepsin extraction from bovine flexor tendon as described by Vogel et al (12).

EXAMPLE 4

Electrophoresis

SDS-PAGE was performed as described by Laemmli (13) using 3–16% linear gradient gels. Gels were stained with silver according to the method of Morrisey (14) omitting glutaraldehyde. Reduction was performed by adding 2-mercaptoethanol to 0.2% v/v to samples prior to electrophoresis and boiling for two minutes.

EXAMPLE 5

ELISA

Antigen was coated to polystyrene 96-well microtiter plates (NUNC immunoplate I, NUNC, Roskilde, Denmark). Fractions from the columns were coated over night under non denaturing conditions using 0.05M sodium carbonate buffer at pH 9.6 containing 0.05% sodium azide. This was followed by incubation for 1 hour with the same buffer also containing 2% bovine serum albumin (blocking buffer) to prevent non specific binding. Collagen I was coated under denaturing conditions using 6M guanidine-HCl, 0.05M Tris-HCl pH 7.4 over night. In this case incubation with blocking buffer was not needed. Sera were diluted in 0.01M phosphate pH 7.5, 0.15M NaCl, 0.05% Tween 20 and 0.25M guanidine-HCl and incubated for 1 hour in the coated microtiter plate. Iqa antibodies were detected by incubation with affinity purified anti human IgA alkaline phosphatase conjugate (Dako) for one hour. Fibronectin was detected using rabbit anti human fibronectin antiserua (Dako) followed by anti rabbit-IgG alkaline phosphatase conjugate (Dako). Enzyme activity was determined using p-nitrophenyl phosphate as the substrate. Microtiter plates were rinsed between each step with 0.15 M NaCl containing 0.05% Tween 20. All samples were analysed as triplicates. Absorbance was sonitored at 405 nm using a Titertek Multiskan photoseter.

EXAMPLE 6

Immunoblotting

Proteins were separated using SDS-PAGE and electrophoretically transferred to nitrocellulose paper (Schleicher and Schüll,-Dassel,W. Germany) at 0.5 A for 4 hours. Non specific binding was prevented by incubation with blocking buffer for 1 hour. IgA antibodies were detected using peroxidase conjugated anti human IgA antiserum (Dako) and fibronectin was detected using rabbit anti human fibronectin followed by peroxidase conjugated anti rabbit antiserum. Enzyme activity was determined with $H_2O_2$/diaminobenzidine (0.5 mg/al) (Fluka) in 0.05M sodium phosphate pH 7.5 containing cobalt chloride and ammonium nickel sulfate (15).

EXAMPLE 7

Isolation of CNBr-fragments

Since we have previously found that IgA antibodies from patients with IgA nephropathy bind to collagen I,II and IV (1) an attempt was made to isolate the specific epitope of bovine collagen I responsible for the binding. Pepsin extracted collagen I was fragmented by the use of CNBr and the fragments were separated by cation exchange chromatography on a Mono S column followed by gel chromatography on a TSK 83000SW column. Binding of antibodies to collagen I could be completely inhibited by fragments identified as the CB7 fragment of the $alfa_1$ chain and the CB3,5 fragment of the $alfa_2$ chain.

These fragments are known to contain the fibronectin binding domain (16). Thus, it appears that fibronectin is involved in the binding of IgA antibodies to collagen. Indeed, as we found for patient IgA antibodies, Engvall et al (8) have previously shown that fibronectin binds to both collagens I and II and that binding is enhanced when denatured collagens are used. In, further support we could demonstrate by ELISA that anti fibronectin antibodies coated to a microtiter plate caused binding of IgA antibodies as well as fibronectin when incubated with serum from patients with primary IgA nephropathy.

When using serum from healthy blood donors as control no IgA antibodies were bound to the anti fibronectin antibody coat. We therefore decided to purify the complexes, in principle using affinity columns for fibronectin and IgA, respectively, in sequence.

EXAMPLE 8

Adsorption of fibronectin to heparin-Sepharose

Figure 1B:
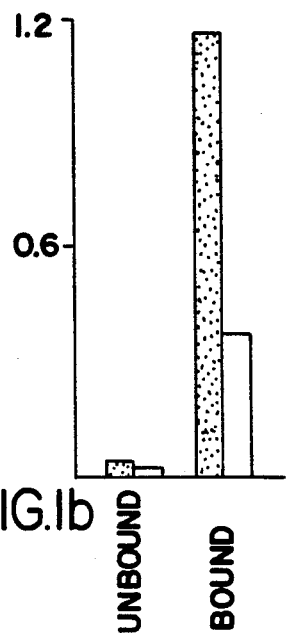
FIG. 1b shows the binding of fibronectin (FN) to a heparin-Sepharose column.
Figure 1C:
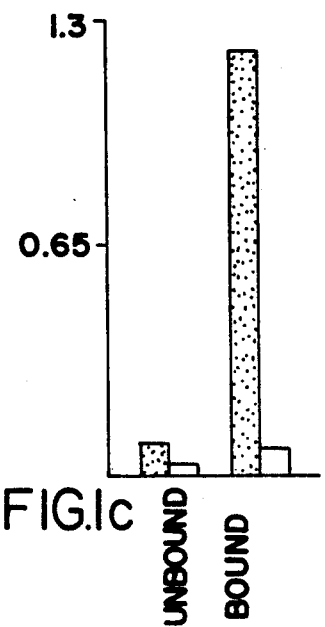
FIG. 1c shows the binding of the IgA-FN complex to a heparin-Sepharose column.

Heparin-Sepharose (9) was used as the initial step for the purification of fibronectin-IgA complexes from human serum. As demonstrated in ELISA (FIG. I), using the fractions as coat, expectedly most of the IgA antibodies were not retained on the heparin column. The fibronectin bound to the heparin column, and was eluted using 0.5M NaCl (FIG. 1).

It is known that fibronectin binds to collagen by its collagen binding domain located in the N-terminal part of the molecule (7,17). The collagen binding properties of fibronectin were utilized in an ELISA to demonstrate the presence of fibronectin-IgA immune complexes in the elute from the heparin column. Denatured collagen I (17) was used as coat. Fractions from the heparin-Sepharose column were incubated in the collagen coated microtiter wells. Bound IgA antibodies were detected using a specific antibody conjugate (FIG. 1). Only the fraction eluted from the heparin column by the use of NaCl contained antibody reactivity in the assay, apparently representing fibronectin-IgA immune complexes in which the IgA antibodies are bound to fibronectin and fibronectin mediates binding to collagen by its collagen binding domain.

The major portion of the IgA antibodies did not bind to the heparin sepharose and no collagen binding IgA antibodies were found in this unbound fraction.

Contrasting results were obtained with a serum sample from a healthy blood donor. No immune complexes were detected neither in the fraction bound to the heparin-Sepharose nor in the unbound fraction (FIG. 1).

EXAMPLE 9

Binding of immune complexes to anion exchange column

Figure 2:
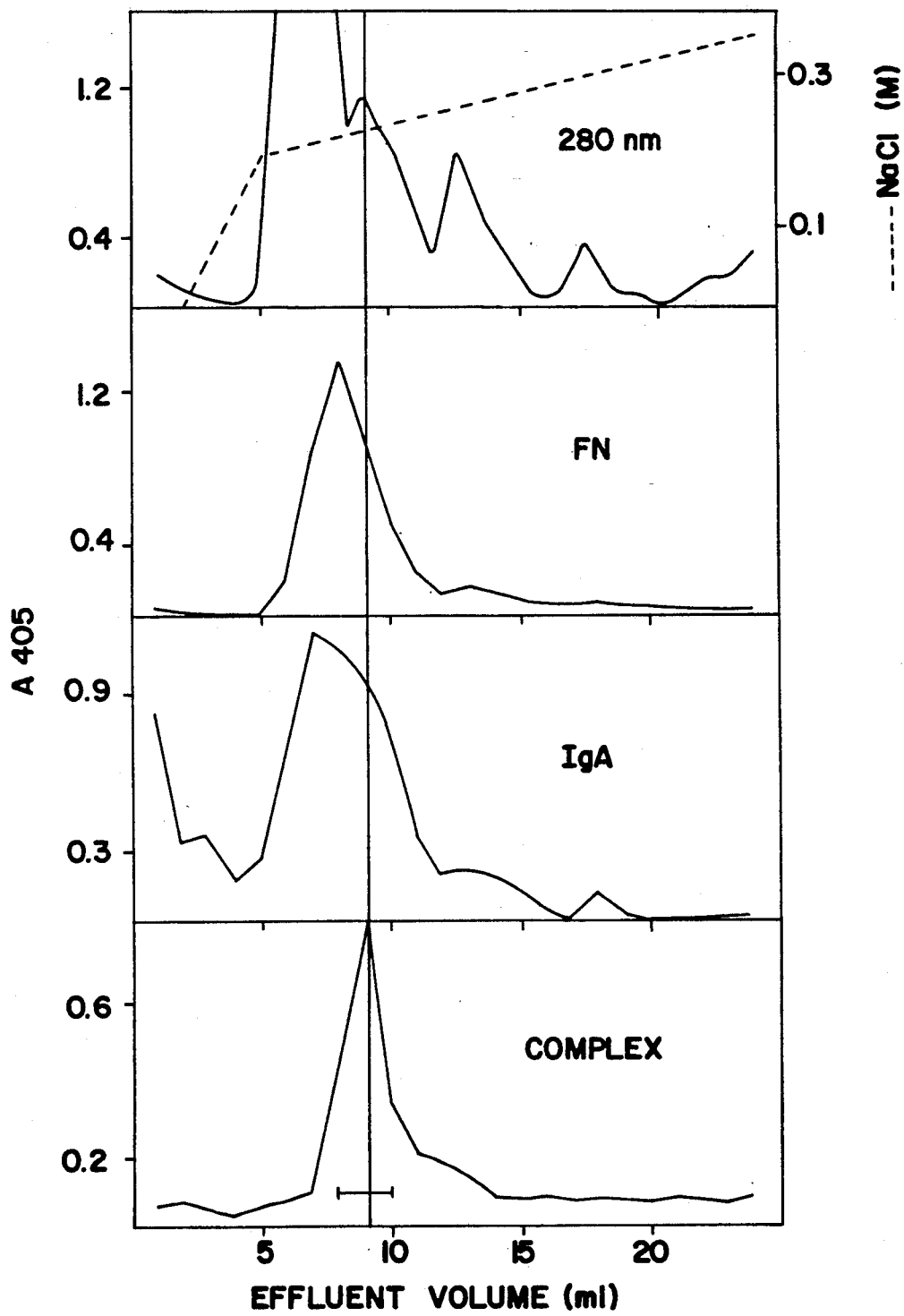
FIG. 2 shows a diagram on the elution of proteins from an ordinary ion exchanger using a salt gradient.

Since heparin binds not only fibronectin, but other plasma proteins as well (9) an ion exchange column was selected for the next step in the purification procedure. Material eluted from the heparin column was applied to a Mono Q, anion exchange, HPLC column. Immune complexes, detected by the ELISA with collagen I coat, were eluted between 0.22–0.24M NaCl (FIG. 2). The presence of free IgA antibodies (separated from the immune complexes) demonstrates that a small proportion of the IgA binds to the heparin column and/or IgA is liberated due to dissociation of immune complexes during the purification procedure.

EXAMPLE 10

Adsorption of the IgA component in immune complexes to jacalin-Sepharose

Figure 3A:
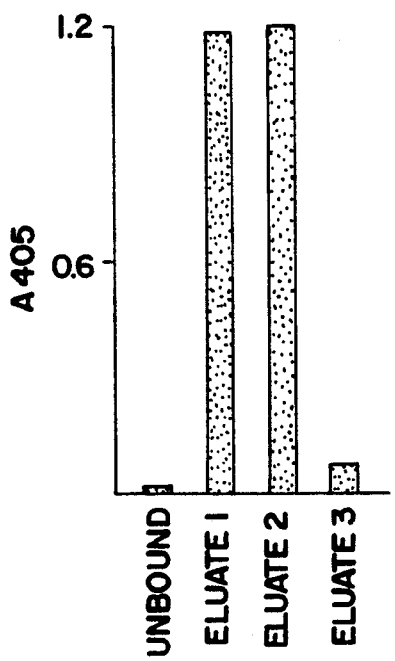
FIG. 3a shows the binding of IgA to a jacalin-Sepharose column.
Figure 3B:
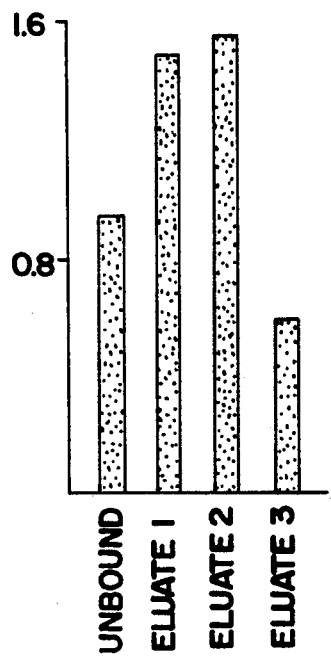
FIG. 3b shows the binding of fibronectin (FN) to a jacalin-Sepharose column.
Figure 3C:
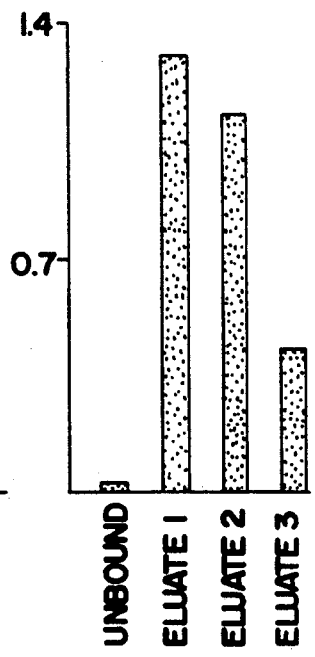
FIG. 3c shows the binding of IgA-FN complex to a jacalin-Sepharose column.
Figure 4A:
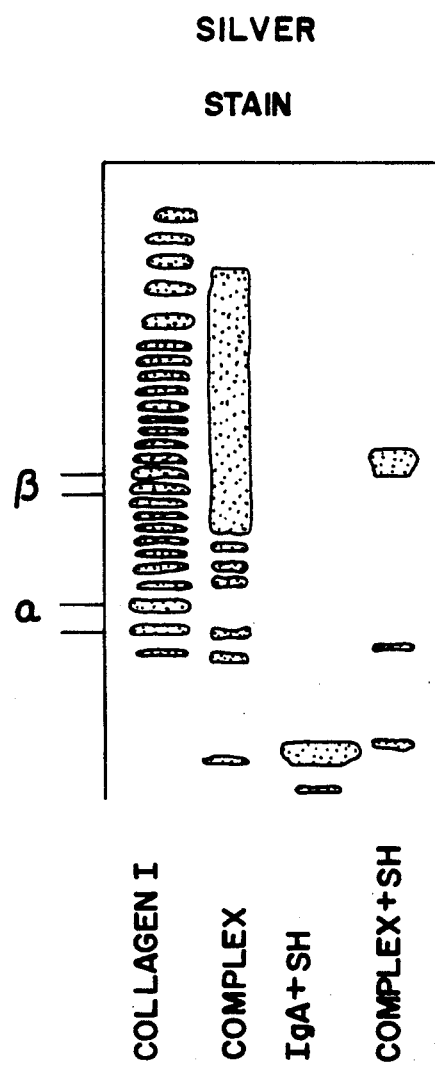
FIG. 4a shows the separation of proteins using SDS-PAGE.
Figure 4B:
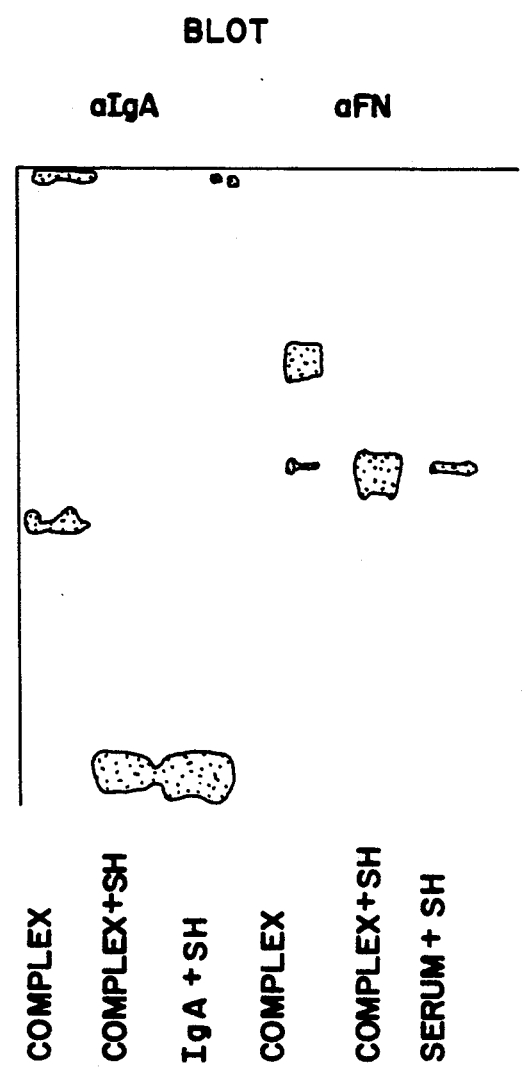
FIG. 4b shows the separation of proteins using immunoblotting.

Fractions containing immune complexes (FIG. 2) were pooled and chromatographed on a jacalin-Sepharose column. Jacalin is a lectin that can be used for binding of IgA antibodies (18). This provides a possibility to separate the complexes from free fibronectin since this structure is not present on the fibronectin molecule. As expected fibronectin is found both in the material not bound to the jacalin column and in the bound fraction that was eluted with melibiose, while IgA antibodies are present only in the bound material (FIG. 3). The fibronectin component of the immune complexes was bound to collagen I in an ELISA and fibronectin and IgA antibodies were identified (FIG. 3). The presence of components with mobilities corresponding to fibronectin and IgA in the material bound to the jacalin column was further demonstrated with SDS-PAGE both with and without reduction (FIG. 4). Further proof for the identity of the components was obtained by immunoblotting using anti-IgA and anti-fibronektin respectively (FIG. 4). The major components visualized by SDS-PAGE was thus shown to represent IgA and fibronectin, respectively.

The above examples show that patients with IgA nephropathy have circulating immune complexes containing fibronectin and IgA antibodies. This is in agreement with a proposed immune complex mediated nature of primary IgA neprhopathy (11).

REFERENCES

1. Cederholm, B., Wieslander, J. and Heinegård, D. (1986) Proc. Natl. Acad. Sci. USA 83, 6151–6155.
2. Mustonen, J., Pasternack, A., Helin, H. and Nikkilä, M. (1985) Am. J. Nephrol. 5, 150–157.
3. Baart De La Faille-Kuyper, E., Kater, L., Kuijten, R., Kooiker, C., Wagenaar, S., Van Der Zouwen, P. and Mees, E. (1976) Kidney Int. 9, 424–429.
4. Nomoto, Y., Sakai, H. and Arimori, S. (1979) Am. J. Clin. Pathol. 71, 158–160.
5. Sakai, H., Nomoto, Y. and Arimori, S. (1979) Clin. Exp. Immunol. 38, 243–298.
6. Sakai, H., Endoh, M. and Tomino, Y. (1982) Clin. Exp. Immunol. 50, 77–82.
7. Hakomori, S., Fukuda, M., Sekiguchi, K. and Carter, W. (1984) In: Extracellular Matrix Biocemistry. Elsevier Science Publishing Co, New York, USA, 229–275.
8. Engvall, E., Rouslahti, E. and Miller, E. (1978) J. Exp. Med. 147:2, 1584–1595.
9. Yamada, K (1982) Immunochemistry of the Extracellular Matrix 1, 111–123.
10. Pettersson, E. and Colvin, R. (1978) Clin. Immunol. Immunopathol. 11, 425–436.
11. Coppo, R., Basolo, B., Piccoli, G., Mazzucco, G., Bulzomi, M., Roccatello, D., De Marchi, M., Carbonara, A. and Di Belgiojoso, B. (1984) Clin. Exp. Immunol. 57, 583–590.
12. Vogel, K., Paulsson, M. and Heinegård, D. (1984) Biochem. J. 223, 587–597.
13. Laemmli, U. (1970) Nature (London) 227, 680–685.
14. Morrisey, J. (1981) Anal. Biochem. 117, 307–310.
15. De Blas, A. and Cherwinski, M. (1983) Anal. Biochem. 133, 214–219.
16. Yamada, K., (1983) Ann. Rev. Biochem. 52, 761–799.
17. Engvall, E. and Rouslahti, E. (1977) Int. J. Cancer 20, 1–5.
18. Roque-Berreira, M. and Campos-Neto, A. (1985) J. Immunol. 134, 1740–1743.

We claim:

1. A method for the diagnosis of IgA nephropathy by detecting fibronectin-IgA complex using a specific binding reaction, comprising the steps:
   a) preparing a solid support capable of specifically binding fibronectin or IgA,
   b) contacting said solid support with a sample of body fluid drawn from a patient to bind fibronectin-IgA complex present in said sample to said solid support by binding one member of said fibronectin-IgA complex to said solid support, and
   c) determining the presence of said complex bound to said solid support by adding a specific binding reagent which binds to the other member of said fibronectin-IgA complex not bound to said solid support in step b).

2. A method according to claim 1, comprising preparing a solid support to bind to the fibronectin portion of said fibronectin-IgA complex wherein said support is coated with a substance selected from the group consisting of collagen, fibrin, and heparin.

3. A method according to claim 1, comprising preparing a solid support to bind to the fibronectin portion of said fibronectin-IgA complex wherein said support is coated with an anti-fibronectin substance.

4. A method according to claim 1, comprising preparing a solid support to bind to the IgA-part of the said fibronectin-IgA complex wherein said support is coated with an anti-IgA or IgA-binding lectin substance.

5. A method according to any preceding claim, wherein said body fluid is human blood, serum, plasma or saliva.

6. The method according to claim 1 wherein said complex bound to said solid support is measured quantitatively using a label which is a radioactive isotope, a fluorescent moiety or a reagent which is part of an enzyme detection system.

7. A method according to claim 2 or 3, comprising binding the IgA-part of said complex to an enzyme-labeled anti-IgA or IgA-binding lectin.

8. A method according to claim 4, comprising binding the fibronectin part of said complex to an enzyme-labeled anti-fibronectin, heparin, fibrin, or collagen.

9. A method according to claim 1, wherein said solid support is a microtiter plate.

10. A diagnostic kit for use in the diagnosis of IgA nephropathy by detecting fibronectin-IgA complex, comprising:
  a) a solid support wherein anti-IgA or an IgA-binding lectin is attached to the surface of said support, and
  b) a specific binding reagent conjugated to a label, wherein said specific binding reagent is heparin, collagen, fibrin or anti-fibronectin and wherein said label is a radioactive isotope, a fluorescent moiety or a reagent which is part of an enzyme detection system.

11. A diagnostic kit for use in the diagnosis of IgA nephropathy by detecting fibronectin-IgA complex, comprising:
  a) a solid support wherein anti-IgA or an IgA-binding lectin is attached to the surface of said support,
  b) a specific binding reagent, wherein said specific binding reagent is heparin, collagen, fibrin or anti-fibronectin, and
  c) an antibody which specifically binds to said specific binding reagent, said antibody conjugated with a label wherein said label is a radioactive isotope, a fluorescent moiety or a reagent which is part of an enzyme detection system.

* * * * *

UNITED STATES PATENT AND TRADEMARK OFFICE
CERTIFICATE OF CORRECTION

PATENT NO. : 5,139,932

DATED : Aug. 18, 1992

INVENTOR(S) : Bo Cederholm, Jörgen Wieslander, Per Bygren, Dick Heinegard

It is certified that error appears in the above-identified patent and that said Letters Patent is hereby corrected as shown below:

```
Title Page, [30] Foreign Application Priority Data; "8701905"
    should read -- 8701905-5 --.
Column 3, line 39; "jacaline a" should read
    -- jacaline agarose --.
Column 5, line 16; "elute" should read -- eluate --.
```

Signed and Sealed this

Twenty-first Day of September, 1993

Attest:

BRUCE LEHMAN

Attesting Officer

Commissioner of Patents and Trademarks